(12) United States Patent
Lall et al.

(10) Patent No.: US 7,595,079 B2
(45) Date of Patent: Sep. 29, 2009

(54) NUTRITIONAL CONJUNCTIVE SUPPORT THERAPY FOR RECOVERY IN ANIMALS FOLLOWING STRESS OR ILLNESS

(75) Inventors: Rajiv Lall, Menomonie, WI (US); Daniel J. DuBourdieu, Limerick, ME (US); Vijayaragavan Sasidharan, Eauclaire, WI (US)

(73) Assignee: Bomac Vets Plus, Inc., Knapp, WI (US)

( * ) Notice: Subject to any disclaimer, the term of this patent is extended or adjusted under 35 U.S.C. 154(b) by 158 days.

(21) Appl. No.: 11/177,411

(22) Filed: Jul. 8, 2005

(65) Prior Publication Data

US 2007/0009502 A1    Jan. 11, 2007

(51) Int. Cl.
*A61K 9/00* (2006.01)
*A61K 36/00* (2006.01)
*A61K 33/00* (2006.01)
*A23K 1/00* (2006.01)

(52) U.S. Cl. .................. 426/635; 424/400; 424/600; 424/725; 424/93.45; 424/93.51

(58) Field of Classification Search ................. 426/635; 424/400, 93.45, 93.51, 600, 725; 435/252.9, 435/254.2

See application file for complete search history.

(56) References Cited

U.S. PATENT DOCUMENTS

| 5,501,857 | A | 3/1996 | Zimmer |
| 5,968,810 | A * | 10/1999 | Fujimura et al. ......... 435/255.1 |
| 6,159,506 | A | 12/2000 | Bieser et al. |
| 6,387,419 | B1 | 5/2002 | Christensen |
| 6,682,762 | B2 | 1/2004 | Register |
| 6,743,770 | B2 | 6/2004 | Bell et al. |
| 6,777,396 | B2 | 8/2004 | Shinzato et al. |
| 2005/0281792 | A1* | 12/2005 | Short et al. .............. 424/93.45 |
| 2006/0228448 | A1* | 10/2006 | Boileau et al. ................ 426/61 |

FOREIGN PATENT DOCUMENTS

| EP | 0519458 A1 * | 12/1992 |
| WO | WO 03/043440 * | 5/2003 |

OTHER PUBLICATIONS

Benyacoub J. et al. (2003) Supplementation of food with *Enterococcus faecium* (SF68) stimulates immune functions in young dogs. Journal of Nutrition 133:1158-1162.
Biourge V. et al (1998) The use of probiotics in the diet of dogs. Jr. of Nutrition 128:2730S-2732S.
Blikslager A. et al. (2001) Glutamine transporter in crypts compensates for loss of villus absorption in bovine cryptosporidiosis. Am J. Physiolo. Gastrointest. Liver Physiol. 281:G645-G653.
Brooks HW et al (1997) Evaluation of a glutamine-containing oral rehydration solution for the treatment of calf diarrhea using an *Escherichia coli* model. Vet J. 153:163-170.
Brooks HW et. al. (1998) Detrimental effects on villus form during conventional oral rehydration therapy for diarrhoea in calves; alleviation by a nutrient oral rehydration solution containing glutamine. The Veterinary Journal 155:263-274.
Campbell, C.G, E.C. Titgemeyer, R.C. Cochran, T. G. Nagaraja and R. T. Brandt, Jr. (1997). Free amino acid supplementation to steers: Effects on ruminal fermentation and performance. J. Anim. Sci. 65:1167-1178.
Carlson SJ (2004) Current nutrition management of infants with chronic lung disease. Nutrition in Clinical Practice 19:581-586.
Center SA (1998) Nutritional Support for dogs and cats with hepatobiliary disease. The Jr. Of Nutrition 128: 2733S-2746S.
Duggan C., Gannon J. and Walker WA (2002) Protective nutrients and functional foods for the gastrointestinal tract. The American Journal of Clinical Nutrition. 75: 789-808.
Friend TH (2000) Dehydration, stress and water consumption of horses during long distance commerical transport. J Animal Science 78:2568-2580.
Halseth AE, et al. (1998) Regulation of hepatic glutamine metabolism during exercise in the dog. Am. J. Physiol. Endocrinol. Metab. 275:E655-E664.
Hutcheson David (1984) Combating transportation stress. Feedlot Management. Oct. p. 10-11.
Krehbiel C.R., S.R. Rust, G. Zhang, and S.E. Gilliland. (2003). Bacterial direct-fed microbials in ruminant diets: Performance response and mode of action. J.Anim, Sci. 81 (E. Suppl.2):E120-E132.
Meier-Hellmann A, Reinhart K, Bredle D and Sakka SG. 2001 Therapeutic options for the treatment of impaired gut function. J Am Soc. Nephrol 12:S65-S69.
Mizock BA, and DeMichele SJ (2004). The acute respiratory distress syndrome: role of nutritional modulation of inflammation through dietary lipids. Nutrition in Clinical Practice 19:563-574.
Price, D (1984) The rumen in the feedlot. Feedlot Management. Oct. p. 16.
Reecy JM et al. (1996) The effect of postruminal amino acid flow on muscle cell proliferation and protein turnover. J. Animal Science 74:2158-2169.
Sato H (1994) Plasma ketone levels in neonatal calves fed medium chain triglycerides in milk. J Vet Med Sci. 56:781-782.
Thorne, James (1985) Why vaccines sometimes fail. Feedlot Management. May 1985, p. 15-17.

(Continued)

*Primary Examiner*—Ruth A Davis
(74) *Attorney, Agent, or Firm*—Charles S. Sara, Esq.; Dewitt, Ross & Stevens, S.C.

(57) ABSTRACT

A composition of probiotics, vitamins and minerals, electrolytes with glutamine and glucose along with medium chain triglycerides are provided as a supplement to animals. This is administered to cattle, calves, sheep, pigs, horses, dogs, and cats that are experiencing stress and or are undergoing medical drug therapy to treat conditions of diseases along with pre and post operative surgical conditions. The composition helps correct imbalances in beneficial bacteria, provides energy and helps in rehydration to reduce recovery time from stress or in disease treatment in these animals.

1 Claim, No Drawings

OTHER PUBLICATIONS

Weese JS and Arroyo L. (2003) Bacteriological evaluation of dog and cat diets that claim to contain probiotics. Can Vet J. 44:212-215.

Young VR and Ajami AM (2001) Glutamine: the emperor or his clothes? Jr. of Nutrition 131:2449S-2459S.

Zaloga GP (2005) Improving outcomes with specialized nutrition support. Jr. of Parenteral and Enternal Nutrition 29:S49-S52.

Rhoads, JM et al. (1992) L-Glutamine with D-glucose stimulates oxidative metabolism and NaCl absorption in piglet jejunum. American Physiological Society G960-964.

A vitamin boost for incoming calves. Feedlot Management, May 1986.

Laflamme, DP (1998) Use of Medium Chain Triglycerides in Clinical Nutrition. Purina Research Report (6 pages).

Wu, G et al. (1996) Dietary Glutamine Supplementation Prevents Jejunal Atrophy in Weaned Pigs. American Institute of Nutrition (7 pages).

Rhoads JM, et al. (1990) Development of L-glutamine-stimulated electroneutral sodium absorption in piglet jejunum. American Physiological Society, p. G99-G107.

Tannuri U, et al. (2000) The Effects of Glutamine-Supplemented Diet on the Intestinal Mucosa of the Malnourished Growing Rat. Rev. Hosp. Clin. Fac. Med. S. Paulo 55 (3):87-92.

* cited by examiner

NUTRITIONAL CONJUNCTIVE SUPPORT THERAPY FOR RECOVERY IN ANIMALS FOLLOWING STRESS OR ILLNESS

CITED REFERENCES

Bibliographies of the references cited can be found at the end of the specifications for this patent application.

FIELD OF THE INVENTION

This invention relates to methods of treating animals for stress by administration of therapeutic levels of species-specific microorganisms, electrolytes with glutamine and energy from glucose and medium chain triglycerides as nutritional support.

DESCRIPTION OF THE PRIOR ART

Nutritional support has become an important therapeutic intervention for improving outcomes in animals undergoing stress. Discoveries about nutritional therapy indicate the importance of providing supplements to animals undergoing normal medical treatment, as well as any comprehensive treatment strategy. Current research reveals that good nutrition can prevent many disease states, and it has also made clear that proper supplementation, if given by the veterinarian, can actually reduce the recovery time during the medical treatment of various diseases, injury or other stressful situations. It is now known that specific nutrients can be used to reduce the effects of these generalized stresses that can include dehydration, loss of energy and imbalance of beneficial bacteria in animals. Addressing these stresses can enhance healing subsequent to surgery and disease and help drugs work more effectively.

Numerous studies have documented the effects of a patient's nutritional status and outcome during infections or stress. Stress can result from many sources, including travel, cold weather, rigorous exercise or the more drastic medical emergencies of infections and injury. Regardless of the source, the animal will go through similar stages in reacting to stress. These stress stages in animals has been recognized since the early half of the twentieth century (Selye 1946). For example, horses and cattle suffer similar stresses during transportation (Friend 2000). When these animals are transported, they can become dehydrated, depleted of energy and have imbalances of bacteria in the gut. Small animals can also be affected in a similar manner during transportation. As such, the reaction to these general stresses for all animal species appears to be quite similar. Other stress factors such as diseases, trauma or surgery can produce a hypermetabolic state characterized by an increase in protein catabolism, and impairment of immune defenses (Center 1998). A sick or injured animal that does not receive sufficient calories will lose muscle in contrast to a healthy animal that will lose primarily fat. Muscles do more than just move animals. Muscles are also stored energy and animals will "cannibalize" this tissue during stress to get at that stored energy. This loss of muscle or lean body mass in the sick or injured patient adversely affects wound healing, immune function, strength (both skeletal and respiratory muscle), and ultimately, prognosis. While it takes time, ultimately, a goal is to correct this muscle loss through stimulation of the appetite by using appropriate methods, although this may be a problem if the gastrointestinal tract (GI) tract is not functioning properly.

Other stresses from digestive disorders are also or problem in animals and can lead to many serious problems for the animal. It could be said that the health of an animal starts with the digestive tract. The gastrointestinal tract has two main purposes: to act as a barrier to the external environment and pathogenic microorganisms, and to act the main portal of entry for nutrients. Nutritional support can be provided by either parenteral or enteral routes. Whenever possible, enteral nutrition is the method of choice, as it reduces complication rates and is known to improve outcome. The benefits of enteral nutritional support go beyond simply meeting basic energy requirements of the animal. It is known that the digestive system modulates the immune system and subsequent inflammatory responses but the digestive system also modulates endocrine/hormonal systems. As such, direct support of the digestive system via enteral nutrition can be a valuable support tool for a variety of important aspects in the treatment regimen of critically ill patients.

One of the generalized responses to stress by animals occurs in the GI tract whereby a decrease in mucosal blood flow can occur and thereby compromise the integrity of the mucosal barrier. This can lead to numerous issues including hemorrhage and sepsis in the animal and it may be difficult to achieve the goal of stimulating appetite without repairing the GI tract first.

There are other aspects to consider in dealing with extended stress on the animal during an infection, surgery etc. The whole digestive system has a delicate balance between bacteria that have numerous beneficial roles in the animal and pathogenic bacteria that are deleterious. This balance will be lost during periods of stress. The way to quickly correct this imbalance is by adding back beneficial bacteria as a supplement to recolonize the gut. Stress also leads to electrolyte and water loss in the body. This dehydration of the animal is another key factor that needs to be corrected quickly if recovery of the animal is to be ensured. The way to correct this dehydration is through supplementation with electrolytes, using specific water enhancing re-absorption mechanisms. Stress can also lead to impairment of the immune response. One way to improve the immune response is to stimulate the immune system with appropriate factors now found in leading nutritional supplements.

Studies have documented the effects of cattle nutritional status and outcome during infections or stress. Some details have been determined on some of the effects in transporting cattle. Dehydration, loss of energy, imbalances of beneficial bacteria and weakened immune systems are common problems in transported animals. Studies on transportation stress on feeder calves have determined that loss of 5-15% body weight commonly occurs depending on rail or truck transport (Hutcheson, 1984). In addition, it is not unusual for calves to arrive at the feedlot with only 10-25% of a normal rumen microorganism's population (Price 1984, Loerch and Fluharty 1999). Loss of water, loss of energy, a reduced microorganism population in the animal, and a weakened immune system are just a few of the contributing factors that lead animals to the sick pen.

These consequences of relocation/shipping can result in increased susceptibility to viral infection in cattle. Viral infection weakens the immunity of the already stressed animals, which, in turn, leads to secondary bacterial infections and further complications for the sick pen. An example of this type of stress for transported cattle is one of the major problems in the beef industry, bovine respiratory disease complex (BRD). BRD is the leading cause of illness and death in feedlots (APHIS 2001). A typical scenario for the development of BRD begins with weaning followed by the transportation of the cattle to the feedlot. The stress of transportation for long distances in crowded conditions, possibly through inclement weather without feed or water, causes the animal to become dehydrated and deprived of energy. As new animals are mixed together in transport they become exposed to new microorganisms that they haven't had a chance to develop immunity against. The defining characteristic of BRD occurs in a group of bacteria and viral organisms known as commensals that normally inhabit the respiratory tract without risk to the animal as long as the animal is healthy and well nourished. Transportation places stresses on the cattle, which will result in alterations in the populations of the commensals in the respiratory tract of cattle. This alteration of commensal population leads to BRD. If the animal is pulled in the early stages of BRD and treated with antibiotics, the prognosis is good for the animal. However if the infection has been allowed to progress further, the animals may not respond as well to antibiotics and may even die.

BRD has a huge economic impact on the cattle industry worldwide. It is called a disease complex because it involves many different components including environmental factors, host factors, viruses, bacteria and other infectious agents. There is no one single cause of BRD. Pathogens identified in BRD include Pasturella, Haemophilus, Actinomyces, Parainfluenza, Bovine respiratory syncitial virus, Bovine herpes virus (IBR), Bovine viral diarrhea, other viruses, Mycoplasma and Chlamydia. Cows that are affected will show respiratory signs such as fever, depression, anorexia, difficulty breathing, nasal and ocular discharge, coughing, sneezing, gasping, grunting, recumbence and death. Animals may stand with their elbows abducted and their necks extended in an attempt to breath.

Treatment consists of appropriate antibiotic therapy to eliminate the bacterial pathogens and supportive therapy or care. Prevention includes vaccinating the dams about 3-4 weeks prior to calving so that calves will have good colostral antibodies when they nurse. Calves should be vaccinated again prior to weaning and being placed in same-age groups. Environmental factors should be controlled such as proper ventilation, humidity, presence of dust and debris, overcrowding, cleanliness, etc. Quarantine of new arrivals should be practiced whenever feasible or an all-in all-out method of management should be adopted.

If the animal requires multiple antibiotic treatments, the value of the animal decreases. It has been reported that the gross value of the carcass is decreased by about $4 for heifer that have undergone one treatment for BRD and $19 for heifers receiving more than one treatment for BRD (Stover et al 2000). Even if these animals do recover and are put back into the regular pen, they usually do not perform well as regular healthy animals. These animals have lower average daily gain and lower marbling scores, resulting in a 37.9% reduction in the percentage of carcasses graded U.S.D.A Choice, or above. Approximately 5 million cattle a year are placed in sick pens due to BRD alone, costing feedlot owners more than $500 million per year to treat them. Depending on the time of year, mortality among the animals can range from 10-15%. This means feedlot owners are losing $50-75 million dollars per year due to mortality alone for BRD, and that money will never be recouped by feedlot owners. Not only that, this financial problem is only going to be worse in the future for feedlot owners because BRD incidences are increasing. To compound matters, it is known that stressed and fatigued cattle don't produce as much immunity as rested cattle when vaccinated (Thorn 1985) despite the availability of better drugs to treat infections. The cost of repulling cattle is going to be even more financially costly. Any supportive therapy in the form of a nutritional supplement to help the drugs and medical treatments for BRD work more efficiently in sick pen cattle will be a welcomed asset to feedlot owners who want to reduce this currently irrevocable $50-75 million dollar yearly financial loss to BRD mortality alone.

These studies have indicated that cattle arriving at the feedlot may not be in the best of shape to allow vaccinations to work properly since they have lost weight, are catabolizing muscle to get more energy, are dehydrated and no longer have the proper balance of microorganisms. The animals in the sick pen are treated with drugs but really should have additional supportive nutritional therapy to address the dehydration, energy, bacterial imbalances issues that also need correction. If these other issues are addressed, then recovery time in the sick pen will be reduced thus putting more animals back into the regular pen and cutting overall cost to the feedlot owner.

It is known that nutrients and nutritional status can affect medication absorption, elimination and tolerance of drugs (Spada 2002, Damle, 2002, Kenyon 1998). Potent antibiotics and other drugs will not function properly if the animal is dehydrated and severely depleted of energy. One of the most important steps in allowing drugs to effectively work in critically ill patients is the establishment of adequate volume status (Meier-Hellmann 2001). If the animal is given replacement fluids and electrolytes and provided with adequate energy, the animal will respond better to the drug therapy. Adequate hydration status allows for vasoactive drugs to circulate properly and become available to the animal and allow for effective action of the drug. In addition, insufficient energy intake will complicate an animal's condition by impairing tissue regeneration and recovery from disease (Center 1998). A primary goal after surgery in horses is to initiate the enteric energy and nutrient uptake (Coenen 2001). This is also true in dogs and cats that contract cancer. It has been shown that diet plays an important role for influencing responses to chemotherapy in dogs (Ogilvie 2003). Among the reasons given for why drugs and vaccines don't always work is related the drugs' inability to work in animals with general overall poor immune and health status. Clearly, it is evident that adequate energy, hydration status and immune status are important in the ability of drugs to function properly.

The current veterinarian approach to dealing with the issues of dehydration, energy loss, bacterial imbalance and immune system for animals in the sick pen or hospital is to treat each of the issues as a separate issue. However this approach is limiting since all of these issues are interconnected. The issues of dehydration, energy loss, imbalance of beneficial bacteria and impaired immune responses resulting from generalized stress or infection need to be addressed as whole concept rather than as individual issues. The new comprehensive approach for the veterinarian to achieve an enhanced rapid recovery and to prevent relapses with specific antibiotics, drug therapy, surgery or other stress should now be to include a supportive nutritional therapy that addresses effective rehydration of the animal, increases in energy, and adding back beneficial bacteria to the gut. This comprehensive approach is going to hold true for small and large animals. This kind of therapeutic approach will help the drugs or antibiotics work more effectively and put the animal back onto a rapid path to recovery along with reducing financial costs incurred by prolonged treatment.

Nutrient Support

There are a number of effective nutrients that play important protective roles in the gastrointestinal tract in animals. Amino acids such as glutamine and arginine, vitamins A, zinc, prebiotics and probiotics have been shown to support a strong role as enteral nutrients in the gastrointestinal health of many animals studies (Duggan 2002). It is clearly evident that proper supplementation with the appropriate nutrients will lead to a functional gut in shorter times for stressed animals and thus faster overall recovery times as the animal regains use of the GI tract. These supplements help accomplish this by addressing adequate energy, hydration status, and the immune status of the stressed animals.

The specific kinds of support that are normally desired with this supplemental nutritional therapy should include rehydration and reenergization of the animal along with the recolonization of the gut with beneficial bacteria. These are the key elements that are most affected during infections or other stressful situations for the animal such as injury, surgery, vaccination, and deworming. It is known in that in these stressful situations a variety of problems can occur including damage to intestinal villi, severe dehydration, inability to absorb nutrients with loss of appetite, overall loss of energy and imbalances of beneficial bacterial normally found in the gut. To treat only the immediate cause with an antibiotic or drug for these problems is not enough. A comprehensive nutritional supplementation approach should be used to: 1) rehydrate the animal by replacing lost fluids and electrolytes in an efficient manner; 2) reenergize the animal with glucose and other energy sources to give the sick animal an energy boost to help fight off the infection and get back to feed and water; 3) recolonize the gut with beneficial bacteria to help restore normal appetite and digestion. If these support issues are addressed, then a number of important steps will occur in the animal naturally, with the help of the drugs, to reduce (i) the severity and length of the initial infection, (ii) the probability of relapse, and (iii) slow weight gain after recovery.

Probiotics

The digestive system of animals contains billions of bacteria, some of which are beneficial, or "good bacteria", and some of which are pathogenic, or "bad bacteria" capable of harming the animal. In a normal healthy animal there is a delicate balance between beneficial and pathogenic bacteria. Normally beneficial bacteria grow more rapidly than pathogenic bacteria viruses, fungi and parasites, depriving these of needed nutrients. Thus, a large majority of the bacteria in the gut are beneficial bacteria which, in turn, make certain important B-complex vitamins, help improve certain normal digestive processes including fermentation of carbohydrates to lactic acid, reduce blood ammonia levels, stimulate the immune system and thus lead to a healthy life in many domesticated animals (Pizzorno, 1996, Friend 1984). However, when there is extended stress on the animal, such as during an infection, surgery etc., the whole system is upset and the delicate balance is lost. The number of beneficial bacteria declines rapidly and the pathogenic bacteria increase in number several fold. Pathogenic bacteria secrete toxins, which lead to illness in the animal, which leads to further stress and further imbalance of the beneficial bacteria. This imbalance will need to be corrected by adding back beneficial bacteria to recolonize the gut.

Direct Fed Microbial (DFM) supplements contain these beneficial bacteria in a stable, viable form. When given as directed they will recolonize the gut by adhering to the intestinal epithelial cells and or in the mucus, thereby helping to increase the number of beneficial bacteria there. Once the beneficial bacteria have begun to recolonize the gut, they will begin competing with the pathogenic bacteria to bring back the normal balance. Several mechanisms have been proposed to be responsible for this interaction, including competition for the adherence sites on the epithelial cells lining the GI tract by the beneficial bacteria that crowd out the pathogenic bacteria or out compete for nutrients. Other mechanisms include poisoning the pathogenic bacteria with antibiotic-like growth-inhibiting factors such as bacteriocins (Klaenhammer 1988) or production of hydrogen peroxide, produced by the beneficial bacteria. As the production of toxins from pathogenic bacteria declines with decline in pathogenic bacteria to tolerable levels, the animal recovers normal appetite and digestion leading to weight gains.

Regardless of the actual mechanisms involved, supplementing with naturally occurring bacteria has been shown to reduce the reinfection rate and intensity for respiratory pathogens in animals. Both aerobic and anaerobic bacteria of the normal flora in the upper respiratory tract can hinder the growth of pathogens and the establishment of a renewed infection. Lack of interfering bacteria facilitates recurrence of these diseases. Recolonizing with naturally occurring beneficial bacteria significantly lowered the reinfections of the upper respiratory tract.

In numerous large animal studies, it has been shown that probiotics have helped cattle with bovine respiratory disease and also gained weight in feedlot situations. Direct fed microbials have been shown in numerous industry and academic studies to be beneficial to both incoming cattle and cattle in sick pens. Industry data on the use of probiotics in incoming cattle generally examines daily weight gain, the number of animals that would get sick, and the cost/benefit ratio (net return) of the product compared to control animals that do not receive probiotics. The preponderance of industry data clearly favors the use of probiotics. For example, studies conducted at Rocky Top Cattle Company (Gerald, 1983) in Oklahoma showed clear daily weight gain and fewer sick animals compared to controls with the use of probiotics. Probiotics at the rate of 10 cc (PROBIOS BOVINE ONE ORAL GEL) was administered to the treatment cattle (N=114) at time of processing. Control animals (N=123) did not receive the probiotic supplement. At the end of 30 days of treatment, the results showed average daily gain (ADG) for the treated animals was 0.72 lb. higher than the control animals. In addition, the probiotic treated animals had far fewer pulled animals than the control group for reasons of health (6 pulls in probiotic group vs. 30 pulls in control group). This study clearly shows that probiotic supplemented animals performed better with greater early gains and much less illness. The typical net return for PROBIOS in 1989 was shown to range anywhere from $13 to $18 per animal, depending on when the use of the probiotics started.

Academic and field studies have also showed the ability of probiotics to reduce the number of times sick pen animals actually have to be treated. In an academic trial (Stewart) when PROBIOS oral gel was administered to cattle at the rate of 10 cc/head, one dose only to incoming cattle, he observed improved weight gain and lower mortality over a period of 30 days. This clearly is a big financial advantage to feedlot owners since treatment and labor costs are reduced and animals will rejoin the general population much sooner. Other studies have also shown similar advantages of using probiotics to enhance weight gain in stressed cattle (Anderson 1992). There are also added advantages of giving direct fed microbials to feedlot cattle which result in decreased fecal shedding of pathogenic *E. coli* 0157:H7 and lowering overall herd susceptibility (Brashears 2003). Clearly the use of probiotics has a place in the feedlot and sickpen.

To maximize the benefits of probiotics, substances known as prebiotics are given as a supplement. Inulin, a complex carbohydrate, is one such prebiotic. Inulin serves as a nutrient for probiotic to stimulate probiotic growth and survival in the gut. The beneficial effects of probiotics may be enhanced and extended by simultaneous administration of a prebiotic (Rolfe, 2000). Prebiotics such as inulin also have additional advantages in that they can also stimulate the immune system. Inulin has been shown to modulate gut associated lymphoid tissue in such a way that antitumoral immunity was stimulated (Pierre 1997). The use of probiotics in other animal species besides cattle has been shown to have beneficial effects for treating stressful events such as transportation, surgery, and antibiotic treatment. In horses, use of probiotics has been shown to be useful for the prevention and treatment of enteric diseases (Weese 2004), reduce pathogenic shedding of pathogenic organisms (Ward, 2004), and enhance growth in neonatal foals and decrease the incidence of diarrhea (Yuyama 2004). While currently available commercial dog and cat foods containing probiotics may not be the best source of probiotics for dogs and cats (Weese 2003), probiotics have been shown to improve digestion in dogs (Biourge, 1998), stimulate specific immune functions in dogs (See table 1: Benyacoup, 2003) and have quicker recovery times for both hospitalized dogs and cats (Barrows 1985, Rastall 2004). The use of probiotics and prebiotics supplementation in small and large animals to help reduce the problems of imbalances of bacteria and to stimulate the immune system are clearly justified in a comprehensive approach to treating stress.

TABLE 1

Probiotic (*Enterococcus facecium*) stimulation of immune system in dogs

|  | Control | Probiotic |
|---|---|---|
| CD21+/MHCII+ B cells (%) | 10.2 ± 1.2 | 17.6 ± 1.8 |
| specific IgA (OD 405 nm) | 0.2 ± 0.01 | 0.35 ± 0.03 |
| specific IgG (OD 405 nm) | 0.5 ± 0.1 | 0.8 ± 0.1 |

(Based on Benyacoub, Jr. Nutrition 133: 1158, 2003).

Energy Issues

When large animals are transported by truck or rail, they must expand more energy to maintain their normal homeostasis (Friend 2000, Marahrens 2003). As animals may have been deprived of food and water during transport or don't want to eat during transport, they can arrive at feedlots being dehydrated and depleted of energy. Upon arrival at the feedlots the animals are subjected castration, dehorning vaccination, deworming, branding, etc. that cause further stress to the animal and even more energy expenditure. This can lead to immune system depression and when the animals come in contact with new animals, the possibility occurs of coming in contact with new infectious agents for which they have no immunity. While most infectious agents may not cause detectable disease in healthy animals, they can express their virulence when the host animal is subjected to severe or prolonged stress, particularly in co-infection with other disease agents. Small animals that are transported to hospitals for surgery can also become stressed and be subject to energy loss. The surgical procedure itself adds stress, and this stress depresses the normal immunological defense mechanisms. These animals can also be exposed to new pathogens to which they have no immunity as they come in contact with other animals at the hospital. It is necessary to treat these animals in a way that will help prevent the spread of disease and also give back energy in the animal.

An easy way to provide quick energy to stressed animals is from an energy supplement containing precursor sources of ATP, which are readily bioavailable for rapid absorption and utilization in the gut. The key to rapid bioavailability is to use the correct kinds of fuel sources in the first place. Nature has seen fit to be use fats, polysaccharides and proteins as the three major starting sources in generating ATP in animals. Glucose is a simple carbohydrate sugar broken down from polysaccharides that has traditionally been, and continues to be, used as a good source of energy in supplements. It is absorbed fast and much is known about the conversion of glucose to ATP. While nature has always been good about using the right sources at the right place, only relatively recently has it been recognized that other fuels besides glucose are utilized even more efficiently in the gut. While using traditional glucose is good, it seems quite reasonable to be using energy sources from the other major starting points of fats and proteins in generating ATP in an energy supplement as well.

Adding a unique energy source of medium chain triglycerides (MCT) to a supplement that takes also advantage of energy from fat sources has also been examined. Fatty acids consist of hydrocarbon chains and a carboxylic acid. They are stored within cells as triglycerides and later released though the blood stream to meet energy demands of various tissues. Long chain fatty acids of 16-20 carbons are normally used by animals for fuels and have been traditionally used in animal feed supplements. However, another chain length exists that will be more effectively utilized for energy production called medium chain fatty acids (MCFA). Medium Chain triglycerides of 6-12 carbons atoms are a fuel source more efficient for ATP production than the long chain fatty acids for some of the following reasons. MCT's are smaller in size and more ionized than the long chain fatty acids and therefore are more soluble and easily absorb in the body by readily crossing cell membranes into the blood stream without any specialized biochemical transport systems that are required by the long chains. As such, when MCTs are hydrolyzed, they are more rapidly and more completely hydrolyzed than long chain fatty acids in the generation of ATP. In addition, MCTs can provide twice as much energy compared to carbohydrate metabolism. MCTs produce 8.3 calories per gram compared to 4 calories per gram of carbohydrates. (Bach 1996).

Because of these unique digestive and metabolic properties MCTs have been examined as energy sources for a number of nutritional settings to give animals additional energy. In neonatal calves (Sata 1994) and adult steers (Sata, 1993) have been shown to be advantageous for increasing ketone and energy levels with the use of MCTs in appropriate concentrations. MCTs have been examined in other animal species studies as well. Dietary MCTs have been effectively absorbed and oxidized by neonatal pigs to improve energy status (Lee and Chiang 1994) and blood glucose (Lepine, 1989), rats (Crozier 1988), chicks (Chiang 1990), and humans (Van Zyl 1996). MCTs have been shown in a number of different animal species to be absorbed, digested and converted to ATP for energy use more efficiently than long chain fatty acids (See Table 2). MCTs are well tolerated by dogs (Grancher D, 1987) and appear to be better caloric source in dogs than long chain triglycerides (Cotter R 1987).

TABLE 2

Medium Chain Triglycerides (MCT) absorption[1], digestiblity[2], and conversion to ATP[3] in horses[1], stressed dogs[2], and stressed piglets[3] compared to control diets with long chain fatty acids

|  | Control diet | MCT diet |
|---|---|---|
| Plasma triglycerides (mmol/l)[1] | 196.7 ± 30.2 | 427.3 ± 85.7 |
| Apparent Digestibility of fat (%)[2] | 27.7 ± 1.3 | 76.8 ± 8.6 |
| Maximal utilization rate (mmol ATP/ kg$^{0.75}$/min)[3] | 0.370.11 | 1.45 ± 0.11 |
| Extent of utilization (mol ATP/kg$^{0.75}$)[3] | 0.23 ± 0.04 | 0.91 ± 0.04 |

[1]Based on Hallebeek, Arch. Tierernahr. 54: 159, 2001.
[2]Based on Laflamme, Purina Research Report, 1998.
[3]Based on Heo, Jr. Nutrition 132: 1989, 2002.

The third principle source of fuel for ATP generation in animals is from protein. Of all of the amino acids that make up proteins, glutamine is the principle circulating amino acid accounting for around 50% of the total exchangeable amino acid pool (Souba. et al. 1985). It had been demonstrated (Gardemann, et al. 1992) that luminal (or enteral) administration of Glutamine enhances glucose absorption. But more importantly it also appears to be the major energy source for the intestinal epithelium (Windmuellar, 1982). Metabolism of Glutamine to alpha-ketoglutarate and subsequent complete oxidation via Kreb's cycle yields 30 moles of ATP per mole of Glutamine. Glutamine is now believed to be a key energy-yielding substrate in reducing stress generating situations of hypoxia, anoxia and dysoxia (Young 2001). In dogs, it is believed that heavy exercise (Halseth 1998), infection, surgery and trauma can deplete the body's glutamine reserves, particularly in muscle cells. In dogs and cats with cancer, it is believed that the addition of glutamine to the diet can be helpful in preventing cancer-induced muscle wasting (Jank, 2004). Glutamine supplementation in dogs appears to preserve body protein from hypercatabolism (Humbert 2002). Glutamine supplementation is now believed to be useful for patients undergoing recovery from major surgery or critical illness (Griffiths R D 1997). There is some evidence for an effect of glutamine supplements in promoting glycogen synthesis in the first few hours of recovery after exercise (Bowtell 1999).

The use of readily absorbed and digestible sources of energy precursors should be the goal of any nutritional supplement. The inclusion of energy sources from carbohydrates, fats and proteins in a predigested format such as glucose, medium chain triglycerides and glutamine is a more comprehensive approach to provide energy to the gut rather than getting it from single source.

Hydration

Glutamine also plays a number of other and perhaps more important roles in animals besides serving as an energy source. The transport of water and electrolytes such as sodium, potassium, chloride and bicarbonate is a key function of the intestinal tract and are fundamental to the hydration status of the animal. Animals in the stressful situations such as antibiotic therapy or surgery require rehydration to enhance and speed up recovery. Traditionally, oral rehydration therapies have used glucose or glycine to promote sodium and water absorption from the gut, which helps combat dehydration and maintain normal acid-base balance. However, a new approach is emerging that it also includes the use of glutamine to promote sodium absorption. One of the important aspects of dehydration [due to diarrhea] in animals is destruction of the intestinal villi tips where sodium absorption normally occurs in an electrogenic manner when using glucose or glycine supplements. Fortunately, nature has provided an alternative electroneutral way of getting sodium into the epithelial cells of the intestinal villus crypts that are not destroyed. Glutamine has the ability and been shown to stimulate sodium uptake and subsequent rehydration using this alternative sodium absorption method in a variety of animals. For example, the use of glutamine in oral rehydration solutions (ORS) has shown positive clinical outcomes for water and electrolyte reabsorption in diarrheic calves compared to conventional ORS. The use of glutamine in an ORS improved plasma volume significantly, corrected packed-cell volume and avoided significant weight loss compared to pre-diarrheic values in an *E. Coli* model of calf diarrhea. (See Table 3: Brooks, 1997). Similar effects have been observed in other animals including rabbits (See Table 3: Silva 1998) and piglets (Rhoads 1991). Glutamine appears to stimulate sodium uptake in calves via crypt cells despite severe villus atrophy in the intestine (Blikslager 2001). Glutamine also increases intestinal villus height in stressed animals (See Table 4), stimulates gut mucosal cellular proliferation and maintains mucosal integrity (Miller, 1999). This regeneration of villi is vital for nutrient absorption and subsequent recovery of the animal. Glutamine has been also been shown to alleviate the detrimental effects of villus form caused by conventional oral rehydration solutions in calves (See Table 4: Brooks 1998). Glutamine treatment has also been shown to be beneficial in repairing oxidant-injured mucosal in horses (Rotting 2004) and oral supplementation of glutamine offers protection to the intestine after surgery in animals (Ramamoorthy, 2003). The addition of glutamine along with electrolytes in the presence of a mixture of amino acids promises to be an effective ingredient beyond the traditional approaches to rehydration.

TABLE 3

Response to Oral Rehydration Solutions (ORS) with or without glutamine in calf[1] and rabbit[2] experimental induced diarrhea.

| | Control ORS | Glutamine ORS |
|---|---|---|
| Plasma Volume (L)[1] | 0.1 ± 0.1 | 0.3 ± 0.1 |
| Blood Volume (L)[1] | 0.0 ± 0.1 | 0.3 ± 0.1 |
| Plasma Sodium (mmol/L)[1] | 2.6 ± 0.7 | 3.8 ± 1.4 |
| Sodium absorption (uEq/g/min)[2] | −0.5 ± .48 | 10.3 ± 1.2 |
| Plasma Volume (L)[1] | −0.012 ± .012 | 0.08 ± 0.008 |

[1]Based on Brooks, Vet. J. 153: 163–170 1997.
[2]Based on Silva, J. Pediatr. Gastroenterol. Nutr. 26: 533 1998.

TABLE 4

Effect of glutamine on intestinal morphology in stressed animals (pigs[1], rats[2], calves[3]).

| | Control Enteral Treatment | With Glutamine | Target value |
|---|---|---|---|
| Jejunum Villus Height (um)[1] | 270 | 358 | ≧339 |
| Jejunum Crypt depth (um)[2] | 244 | 134 | ≦150 |
| Mid plus Distal small intestinal Crypt width (mean % of baseline control)[3] | 111.3 | 92.2 | ≦100 |

[1]Based on G. Wu, Jr. of Nutrition 126: 2578, 1996 (Weaning of pigs).
[2]Based on U. Tannuri, Rev. Hosp. Clin. Fac. Med S. Paulo 55: 87, 2000 (malnourished rats).
[3]Based on HW Brooks, Vet. Jr. 155: 263, 1998 (*E. coli* induced diarrhea in calves).

Immune Stimulation

One of the important factors in rapid recovery from injury, surgery, infections and burns is the adequate nutrition of the immune system and the implications of this for whole body metabolism. Cells in the immune system such as lymphocytes and macrophages undergo increased rates of productions and rapidly increase during inflammatory immune responses. These cells have unique nutritional requirements that require glutamine for purine and pyrimidine nucleotide synthesis needed in cell division (Newsholme 1985) It has become evident that glutamine is used a very high rate by lymphocytes and macrophages (Ardawi 1985, Newsholme 1987). The requirement for glutamine will increase dramatically after injury, surgery, infection and burns since there will be increased activity of the immune system and an increased number of cells will participate in cell division and hence will require glutamine. Glutamine levels in the plasma and tissues pools decline markedly in the course of many different catabolic diseases (Smith 1990) and has been suggested to be a conditionally essential dietary amino acid under conditions of stress (Wischmeyer 2003). It has been shown that glutamine provision corrects or improves the function of some tissues when that function has been impaired in a number of stress generating situations. Glutamine infusion in dairy cows has been shown to result in an increase of blood plasma glutamine (Plaiser 2001). In post-operative dogs (Roth 1988) glutamine-containing dipeptides attenuated or reversed the injury-associated decrease in the concentration of glutamine and in muscle and plasma. In other animals, including man, glutamine provision has been shown to be beneficial for the immune system (Burke 1989, Kweon 1991, Yoshida, 1992, Scheltinga, 1991).

Glutamine promotes secretory IgA production in a way that will improve the immune defense of the gut lining and help prevent infections (Pastores 1994, Souba 1993). Secretory IgA, produced in cells around the mucin secreting glands of the intestinal mucosa, plays a role in binding and inactivating foreign antigens such as virus, fungi, protozoa and pathogenic bacteria. In animals fed a glutamine free diet, secretory IgA falls of dramatically (Averdy, 1990). The overall benefit of providing glutamine supplements to all metabolically compromised animals arises from the multiple anabolic and host protective effects of this amino acid and immunomodulation is only one important facet (Wilmore 1998).

There are a number of other factors for enhancing the immune system. Besides glutamine and probiotics, carbohydrates, lipids, amino acids, minerals, supplemental vitamins and electrolytes should also be provided. Nockels (1996) reported that antioxidants improve immunity in animals following stress. Vitamins act as co-factors in several metabolic pathways and can be depleted in stress generating situations. These should be given back to the animal as a supplement, to provide the immune system the proper building materials for proper function. Addition of Vitamin E, along with other fat and water-soluble vitamins, will help in better utilization of energy and speed up recovery. The natural immunity will start working, leading to much faster recovery from the stress-generating situations. It has been shown that vitamin E and B-complex supplementation results in significant daily gain and improved feed conversion in steer calves starting and receiving diets (Feedlot Management 1986). Hays et al. (1987) found that when Vitamin E was supplemented to newly received steers, it increased daily gain and decreased morbidity and sick days per calf. Galyean et al. (1999) reported that Vitamin E added to receiving diets was beneficial to increasing gain and decreasing BRD Mortality. In another study, Rivera et al. (2002) also concluded that supplemental vitamin E might be beneficial for helping stressed cattle recover from BRD. Vitamin A is a fat-soluble vitamin that plays a vital role in maintaining normal health. It was observed that vitamin A should be increased in stressful conditions like low environmental temperatures or exposure to infective bacteria (Eaton 1972).

Vitamins and minerals work together in a synergistic manner and are essential to life by working in many biochemical functions, thereby contributing to normal and overall health. Deficiencies of specific minerals can result in various metabolic disorders but supplementation can help correct these problems. Galyean et. al. (1999) reported that supplemental Zinc and Copper can alter immune function of newly received calves and some field trials have shown decreases in BRD morbidity rate.

Immune enhancing diets (IED) have been shown to improve wound healing, modulate vascular reactivity, affect gut blood flow, alter endothelia activation, modulate cytokine response and alter neurohormonal signaling and reduce hospital time (Zaloga, 2005). Nutritional management of chronic lung disease been a major medical challenge in humans but guidelines have now been established that show a need for energy, electrolytes vitamins and minerals when treating these cases (Carlson 2004). Pig and rat models of acute respiratory distress syndrome have shown a beneficial role of these types of supplementation to decrease lung inflammation (Mizock 2004). These IEDs have demonstrated beneficial positive clinical effects and yielded economic advantages for health care costs as reduction in hospital time occurs (See Table 5).

TABLE 5

Effect of Immune Enhancing diets on clinical outcomes in critically ill patients. Meta analysis of 26 primary studies of surgical, burn, trauma and medical cases.

| Parameter | Reduced Time | p Value |
| --- | --- | --- |
| Mechanical ventilation time | (−2.3 days) | 0.009 |
| ICU stay | (−1.6 days) | <.0001 |
| Hospital stay | (−3.4 days) | <.0001 |

(Based on Zaloga JPEN 29: S49, 2005).

The supplements that have been discussed are known to have efficacy in cattle, horses, pigs, sheep dogs, cats and other animals when used by themselves. The concept of using probiotics to treat animals that have been stressed by transport or have been place in the sick pen or hospital appears to be valid and accepted by many veterinarians. The clinical studies have shown that cattle fed probiotics gain more weight, have significantly faster recovery time from sick pens and significantly lower reinfection rates than cattle not fed probiotics. The concept of using glutamine with electrolytes in calves and other animals to treat dehydration has been shown to be more effective than standard oral rehydration solutions containing glucose or glycine. In addition, there are other multiple benefits of glutamine for animals under stress situations including intestinal villi repair and serving as an energy source for the GI tract and immune system. The concept of supplementing vitamins and minerals to incoming cattle at feedlots to improve performance, reduce morbidity, and stimulate the immune system is now accepted. In addition, the concept of using glucose, medium chain triglyceride as an energy source has been demonstrated to be an effective way to increase energy levels in cattle, dogs and other animals.

SUMMARY OF THE INVENTION

While all of these supplements appear to be effective by themselves, a new concept has emerged that indicates there are synergistic effects of these supplements when combined together. The issues of dehydration, energy loss, imbalance of beneficial bacteria and impaired immune responses in cattle, horses, dogs and other animals resulting from generalized stress needs to be addressed together rather than as individual issues. In this new approach, the veterinarian achieves enhanced rapid recovery and prevention of relapses by combining specific antibiotics or drug therapy with supportive nutritional therapy, particularly supplements that address effective rehydration of the animal, increases in energy and adding back beneficial bacteria to the gut in a synergistic approach. This kind of therapeutic approach will enhance the therapeutic effect of the drugs or antibiotic by making them work more effectively and putting the animal back onto a rapid path to complete recovery.

By providing the supplemental nutritional support for specific therapies for injury, infections and stress it is known that animals are able to respond to antibiotics and drugs better, the reinfection rate is lower, and animals will regain strength along with normal appetite faster. Use of antibiotics is a key to successfully controlling infections. But, for an antibiotic to perform well and work as intended, helping out the immune system, the overall energy level, the hydration status and balance of beneficial bacteria in the gut of the animal is a must. A comprehensive approach of a supportive nutrition that addresses all of the issues of hydration, energy and the general health of the gut is indicated. It will lead to positive outcomes of antibiotic therapy, surgery or other stressful situations for the animal that will be much faster than if not employed at all.

The present inventors have developed improved nutrient compositions that will reduce recovery time for animals that have had stress placed on them from various sources. In view of the foregoing, it will be appreciated that a composition for improving the outcome of animals undergoing medical treatments of drugs, antibiotic therapy, surgery or other forms of stress would be a significant advancement in the art. It is an object of the present invention to provide compositions for use as a dietary supplement that, when ingested, enhances antibiotic or drug treatment of ailments in the gastrointestinal tract from pathogens such as bacteria, viruses, fungi or protozoa or other causes. It is an object of this invention to provide a composition for uses as a dietary supplement that provides energy for the intestinal enterocytes and immune system lymphocytes turnover. It is an object of this invention to provide as a dietary supplement a composition that effectively rehydrates animals.

The invention provides administration of probiotics and prebiotics, glutamine with electrolytes, glucose and medium chain triglycerides, along with vitamins and minerals in effective amounts to animals that are exhibiting stress. It is expected that this invention will benefit stressed or sick animals by effective rehydration, correcting bacterial imbalances, adding additional energy to the animal, improve the immune system and allow drug or antibiotic therapy a chance to work more effectively. This will result in shorter recovery times for animals under stress or being treated for specific diseases or conditions such as surgery.

It is already known that use of species specific probiotics by themselves will cause weight gain in cattle, and reduce recovery time in the sick pen, and improve overall herd health by reducing fecal shedding of pathogenic organisms. Similar beneficial effects are seen in with the use of probiotics in other animals. The administration of species specific probiotics in horses have been shown to enhance growth in neonatal foals and young horses, be useful in treatment of enteric disease and decrease the incidence of diarrhea, prevent the spread of diseases by reducing shedding of pathogenic organisms in the environment. Likewise, in hospitalized dogs and cats a reduction of digestive disorders and reduced shedding of pathogenic organisms occur, better appetite and faster recovery times also occur with the use of probiotics. In addition, enhanced specific immune functions and intestinal health occur when administrating species specific probiotics in dogs and cats. The use of probiotics in these animal species has clearly been shown to be effective and beneficial in correcting imbalances in intestinal microorganisms, helping animals improve digestive issues and regain homeostasis for faster recovery in stress situations.

The objects and advantages of the invention will appear more fully from the following detailed description of the preferred embodiment of the invention.

DETAILED DESCRIPTION OF THE INVENTION

The nutritive compositions for the present invention are a novel combination of probiotics, prebiotics, glutamine, glucose, glycine electrolytes, vitamins and minerals. These ingredients in combination have a prophylactic and therapeutic effect in maintaining and enhancing gastrointestinal microflora, the rehydration status, energy balance and the immune system. A healthy intestinal environment will enhance the overall health of the mammal since many diseases, no matter what part of the body they manifest themselves, actually start in the GI tract. The nutritive supplement compositions of the present invention contain ingredients in a form that is bioavailable and thus accomplish their important nutritive functions. The nutritive compositions of the present invention function as source of growth and energy factors for the repair and growth of healthy intestinal tissue and cells found in the immune system. These compositions are understood to contain components that enhance the probiotic colonization of the intestinal tracts of animals.

Probiotics

There are a variety of probiotic microorganisms, which are suitable for use in this invention including yeast, such as *Saccharomyces* and bacteria such as the genera *Bifidobacterium, Enterococcus*, and *Lactobacillus*. The invention is not, however limited to these particular organisms. The person skilled in the art would understand and recognize those microorganisms, which may be included in the composition of the invention.

The preferred form for the probiotic composition in this invention for any animal species is to use species of microorganisms that normally inhabit the gut of that particular animal species. For example, in a preferred form the probiotic composition for cattle and calves are selected from *Enterococcus* and *Lactobacillus* species. In a preferred probiotic composition for dogs and cats is *Lactobacillus* species include but not limited to *Lactobacillus acidophilus, Lactobacillus plantrum, Lactobacillus casei* and *Enterococcus* species include *Enterococcus faecium*. The preferred probiotic composition for horses includes but not limited to *Lactobacillus acidophilus, Lactobacillus plantrum, Lactobacillus casei* and *Enterococcus faecium*. The preferred probiotic composition for pigs is *Lactobacillus acidophilus, Lactobacillus plantrum, Lactobacillus casei* and *Enterococcus faecium*. The preferred probiotic composition for sheep is *Lactobacillus acidophilus, Lactobacillus plantrum, Lactobacillus casei* and *Enterococcus faecium*. The probiotics are administered at doses of $10^7$ to $10^{11}$ colony forming units (CFU) per day.

Probiotics and Inulin

The use of inulin or other prebiotic components help enhance the survival rate of the probiotics in the gut of the animal by adding a source of energy specifically designed for the probiotic. This maintains the vitality of the probiotic itself but can have other synergistic and protective effects in the animal when used in combination with a probiotic. The use of prebiotics such as inulin and fructo-oligosaccharides have shown positive effects on the microflora balance in dogs, cats and other animal species and can also help stimulate the immune system. The use of prebiotics like inulin will be quite beneficial to both the probiotic and the animal as well.

Fructo-oligosaccharides

Fructo-oligosaccharides suitable for the present invention may include any fructo-oligosaccharide available for consumption. Preferably the fructo-oligosaccharide may be selected from inulin or soy fructo-oligosaccharide. It will be appreciated by one skilled in the art, however, that other oligosaccharides would also be suitable for inclusion. This would include oligosaccharides including galacto-, malto-, isomalto-, gentio-, xylo-, palantinose-, chito-, agaro-, neoagaro-, alpha-, beta-, gluco-, cyclo-inulo-, glycosylsucrose, lactulose, lactosucrose and xylsucrose. The oligosaccharide can be used in the compositions from concentrations of about 0.01 to 10% (w/w).

Electrolytes

The administration of electrolytes such as sodium chloride and potassium chloride with water is well established to promote rehydration in all animals that have become dehydrated due to scours and diarrhea or from other stress generating situations. The use of glucose or glycine has been proven to promote modest amounts of sodium uptake the animal. However it has been found that glutamine promotes even more effective sodium uptake in a number of animals including pigs and calves. The beneficial effects of glutamine for sodium uptake are even more pronounced by working synergistically in the presence of additional glucose or glycine. The advantages of glutamine to promote sodium uptake in oral rehydration solutions in calves has previously been the subject of an approved patent. Preferably the concentration of sodium per dose for animals is from 5 mg to 100 mg/kilogram of body weight. Preferably the concentration of potassium is from 5 mg to 100 mg/kilogram of body weight. The preferable concentration per dose of glucose is from 10 to 50 grams/kilogram of body weight. The preferable concentration of glycine is 66 mg to 264 mg/kilogram of body weight. The preferable concentration of glutamine is from 44 mg to 100 mg grams/kilogram of body weight.

There are other advantages of glutamine in this invention. Glutamine has been shown to increase intestinal villus height, stimulate gut mucosal proliferation or maintain mucosal integrity in a number of animal species including cattle, horses, pigs, sheep, and dogs. Glutamine provision can protect the GI tract and help repair the GI tract in times of stress for animals. As the GI tract becomes repaired or protected from stress, the ability of the gut will be improved to maintain normal digestive functions. The improved ability of the GI tract to digest food will lead to faster recovery times in during times of stress, whatever the cause may be. This will be become quite beneficial to the overall health of the animal.

Energy Sources

This invention utilizes a comprehensive approach to supplying energy to the stressed animal. Glutamine is the major energy source for the intestinal epithelium, which helps account for some of its important and beneficial actions in the GI tract. However, the other sources of energy come from carbohydrates and fatty acids that help animals quickly regain the energy lost in stress generating situations. This invention uses glucose to help quickly put energy back into stressed animals. Glucose is a simple carbohydrate that animals can quickly and efficiently absorb and utilize to generate ATP required by the animal to carry out biochemical functions. Another source of energy that this invention uses is from medium chain triglycerides. Medium chain triglycerides have an important advantage compared to carbohydrates for ATP production in that considerably more energy is made per molecule. MCTs can provide twice as much energy compared to carbohydrate metabolism. MCT administration has been shown to be beneficial in cattle, calves, dogs and other animal species for readily supplying required energy. This invention will utilize the three sources of energy that nature uses to provide a more balance approach to providing stressed animals required energy. The fatty acids found in the medium chain triglycerides that are preferred in this invention are from 8 to 10 carbon chains in length. The preferable concentration of MCT in this composition is from 100 mg to 600 mg/kilogram bodyweight.

This invention uses glutamine, vitamins and minerals to help stimulate the immune system. Glutamine is known to be required rapidly in dividing cells of the immune system and help reinforce the immune system. Under times of stress, a loss of available glutamine occurs in the animal even as the immune system attempts to respond rapidly. Provision of glutamine in this invention will be beneficial to the immune system by supplementing the requirements of the stressed animal for additional glutamine. This additional glutamine has been shown to be beneficial to cattle, rats, humans, dogs and other species in many types of stress situations.

Vitamins

This invention also uses vitamins to help stimulate the immune system. The use of vitamin A, vitamin E, and folic acid are known make the immune system work in an optimal manner. Deficiencies of vitamin A in animals will lead to degeneration of the mucosa while deficiencies of vitamin E can lead to muscular dystrophy. Deficiencies of folic acid can lead to a reduction in red cell production and subsequent anemias. Deficiencies of vitamin D can lead to problems in absorbing calcium. Provision of vitamins A, $D_3$ and E along with folic acid will benefit stressed animals by enhanced cell-mediated and humoral immune responses and better GI tract maintenance. The per dose preferred concentration for vitamin A is from 50-300 IU/kilogram bodyweight; for vitamin E 0.5 IU/kilogram and folic acid is from 0.5 to 2 IU/kilogram bodyweight. The preferred concentration of vitamin $D_3$ is from 5-30 IU/kilogram.

Minerals

Minerals play important roles in many biochemical functions in the body. Deficiencies of minerals can lead to problems in the immune system. However supplementation of zinc and copper can help correct these problems. As absorption of chelated minerals to amino acids or other substances is enhanced, this invention uses chelated minerals. This invention uses chelated copper, zinc, and manganese to benefit the immune system. The preferred concentration of copper is from 0.1 mg to 2 mg/kilogram; for zinc is from 100 mg to 300 mg/kilogram; and for manganese is from 0.05 mg to 0.2 mg/kilogram.

The synergistic effects of adding the additional components of glutamine with electrolytes, the energy sources of glucose with medium chain triglycerides, and vitamins with minerals will further increase the chances of the animal to gain lost weight and have shorter recovery times. This will result in significant additional profits to animal owners because of the cost effectiveness of this product should result in at least a 3:1 ratio in benefit returned to cost of use.

| I. A typical formulation for adult cattle is: | |
| --- | --- |
| Glycine | 1000 mg |
| Glutamine | 100 mg |
| Sodium(min) | 3.5% |
| Sodium (max) | 3.8% |
| Potassium | 250 mg |
| Vitamin A | 5,000 IU |
| Vitamin $D_3$ | 750 IU |
| Vitamin E | 75 IU |
| Glucose | 3000 mg |
| Zinc | 90 mg |

-continued

I. A typical formulation for adult cattle is:

| | |
|---|---|
| Inulin | 2000 mg |
| Lactic Acid Bacteria[1] | 49 million CFU |

[1]Consisting of a combination of *Enterococcus faecium*, *Lactobacillus acidophilus*, *Lactobacillus plantarum* and *Lactobacillus casei*.

II. A typical formulation for calves is:

| | |
|---|---|
| Glycine | 500 mg |
| Glutamine | 50 mg |
| Sodium (min) | 3.5% |
| Sodium (max) | 3.85% |
| Potassium | 125 mg |
| Vitamin A | 2,000 IU |
| Vitamin $D_3$ | 375 IU |
| Vitamin E | 37 IU |
| Glucose | 1500 mg |
| Zinc | 45 mg |
| Inulin | 1000 mg |
| Lactic Acid Bacteria[1] | 49 million CFU |

[1]Consisting of a combination of *Enterococcus faecium*, *Lactobacillus acidophilus*, *Lactobacillus plantarum* and *Lactobacillus casei*.

III. A typical formulation for dogs and cats is:

| | |
|---|---|
| Glycine | 10 mg |
| Glutamine | 20 mg |
| MCT Fatty acids | 3.0% |
| Sodium (min) | 3.25% |
| Sodium (max) | 3.85% |
| Calcium (min) | 11.0% |
| Potassium | 0.0005% |
| Vitamin A | 1,000 IU |
| Vitamin $D_3$ | 100 IU |
| Vitamin E | 10 IU |
| Ascorbic Acid | 10 mg |
| Riboflavin | 0.5 mg |
| Glucose | 530 mg |
| Zinc | 11.25 mg |
| Inulin | 200 mg |
| Lactic Acid Bacteria[1] | 10 million CFU |

[1]Consisting of a combination of *Enterococcus faecium*, *Lactobacillus acidophilus*, *Lactobacillus plantarum* and *Lactobacillus casei*.

IV. A typical formulation for horses is:

| | |
|---|---|
| Glycine | 20 mg |
| Glutamine | 100 mg |
| MCT Fatty acids | 11.4% |
| Sodium (min) | 5.0% |
| Sodium (max) | 5.75% |
| Potassium | 2.0% |
| Magnesium | 1.8% |
| Vitamin A | 20,000 IU |
| Vitamin E | 200 IU |
| Thiamine HCl | 500 mg |
| Pyridoxine HCl | 400 mg |
| Glucose | 8000 mg |
| Zinc | 90 mg |
| Inulin | 1400 mg |
| Lactic Acid Bacteria[1] | 300 million CFU |

[1]Consisting of a combination of *Enterococcus faecium*, *Lactobacillus acidophilus*, *Lactobacillus plantarum* and *Lactobacillus casei*.

V. A typical formulation for sheep and goats is:

| | |
|---|---|
| Glycine | 500 mg |
| Glutamine | 50 mg |
| Sodium (min) | 3.5% |
| Sodium (max) | 3.85% |
| Potassium | 125 mg |
| Vitamin A | 2,000 IU |
| Vitamin $D_3$ | 375 IU |
| Vitamin E | 37 IU |
| Glucose | 1500 mg |
| Zinc | 45 mg |
| Inulin | 1000 mg |
| Lactic Acid Bacteria[1] | 49 million CFU |

[1]Consisting of a combination of *Enterococcus faecium*, *Lactobacillus acidophilus*, *Lactobacillus plantarum* and *Lactobacillus casei*.

VI. A typical formulation for pigs is:

| | |
|---|---|
| Glycine | 20 mg |
| Glutamine | 100 mg |
| MCT Fatty acids | 11.4% |
| Sodium (min) | 5.0% |
| Sodium (max) | 5.75% |
| Potassium | 2.0% |
| Magnesium | 1.8% |
| Vitamin A | 20,000 IU |
| Vitamin E | 200 IU |
| Thiamine HCl | 500 mg |
| Pyridoxine HCl | 400 mg |
| Glucose | 8000 mg |
| Zinc | 90 mg |
| Lactic Acid Bacteria[1] | 300 million CFU |

[1]Consisting of a combination of *Enterococcus faecium*, *Lactobacillus acidophilus*, *Lactobacillus plantarum* and *Lactobacillus casei*.

Delivery System

The delivery system for calves and adult cattle are in the form of "Boluses". Electrolytes and energy will be packaged in one bolus and the Direct fed microbials will be provided in the second bolus. To differentiate the products, the boluses will be color-coded. "Electrolytes and energy bolus" will be "Pink" in color and the "direct fed microbial" bolus will be "white" in color. One pink and one white bolus make "One dose" or "One feeding".

The delivery system for dogs and cats will be in the form of "Chewable tablets".

Electrolytes and energy will be packaged in one tablet and the Direct fed microbials will be provided in the second tablet. In order to differentiate the products the tablets will be of different "shapes". "Electrolytes and energy tablet" will be "Square" in shape and the "direct fed microbial" bolus will be "round" in shape. One round and one square tablet will make "One dose" or "One feeding". In order to make the tablet palatable the product will be made with liver and fish flavor.

The delivery system for horse will be in the form of a "Non-aqueous gel".

Electrolytes, energy and Direct fed microbials will be delivered in an oil based gel along with preservatives and stabilizers. The product will be packaged in multi-dose or single dose plastic syringes.

While this invention may be embodied in many forms, what is described in detail herein is a specific preferred embodiment of the invention. The present disclosure is an exemplification of the principles of the invention is not intended to limit the invention to the particular embodiments illustrated.

It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Anderson V L (1992) Preconditioning rations: barley vs. barley screenings with and without probiotic fed to range and drylot raised steer calves. North Dakota Farm Research 45:16-18.

Ardawi M S M, Newshome, E A (1985) Metabolism in lymphocytes and its importance to the immune response. Essays Biochem. 21:1-44.

Alverdy, J A. (1990) The effect of total parenteral nutrition in gut lamina propria cells. Jr of. Parenteral and. Enteral. Nutrition. 14: (Supplement).

Animal and plant health inspection service 2001. Treatment of respiratory diseases in U.S. feedlots. Info sheet. Veterinary services (October).

Bach A C and Bahayan V K. (1982) Medium-chain trigylcerides: an update. Am J. Nutri. 36:950-962.

Bach C, Ingenbleek Y, and Frey A. (1996) The usefulness of dietary medium-chain triglycerides in the body weight control: fact or fancy. J of Lipid Research 37:708-726.

Barrows G T, Deam B D. (1985) Using probiotics in small animals: anew approach. Veterinary Medicine 80:41-42.

Benyacoub J. Et al. (2003) Supplementation of food with *Enterococcus faecium* (SF68) stimulates immune functions in young dogs. Journal of Nutrition 133:1158-1162.

Biourge V. et al (1998) The use of probiotics in the diet of dogs. Jr. of Nutrition 128:2730S-2732S.

Blikslager A. Et al (2001) glutamine transporter in crypts compensates for loss of villus absorption in bovine cryptosporidiosis. Am J. Physiolo. Gastrointest. Liver Physiol. 281:G645-G653.

Bowtell J L et. el. (1999) Effect of oral glutamine on whole body carbohydrate storage during recovery from exhaustive exercise. J. Appl. Physiol. 86:1770-1777.

Brashears M M et. Al (2003) Prevalence of *Escherichia coli* 0157:H7 and performance by beef feedlot cattle given *Lactobacillus* direct fed microbials. Jr. Of Food Protection 66:748-754.

Brooks H W et al (1997) Evaluation of a glutamine-containing oral rehydration solution for the treatment of calf diarrhea using a *Escherichia coli* model. Vet J. 153:163-170.

Brooks H W et. al. (1998) Detrimental effects on villus form during conventional oral rehydration therapy for diarrhea in calves; alleviation by a nutrient oral rehydration solution containing glutamine. The Veterinary Journal 155: 263-274.

Burke D J, et al. (1989) Glutamine-supplemented total parental nutrition improves gut immune function. Arch Surg. 124: 1396-1399.

Campbell, C. G, E. C. Titgemeyer, R. C. Cochran, T. G. Nagaraja and R. T. Brandl, Jr. (1997). Free amino acid supplementation to steers: Effects on ruminal fermentation and performance. J. Anim. Sci. 1997 75:1167-1178.

Carlson S J (2004) Current nutrition management of infants with chronic lung disease. Nutrition in Clinical Practice 19:581-586.

Center S A (1998) Nutritional Support for dogs and cats with hepatobiliary disease. The Jr. Of Nutrition 128: 2733S-2746S.

Chiang S H, Huang K H and Le H F (1990) Effects of medium chain triglycerides on energy metabolism, growth and body fat in broilers. J Clin Soc. Anim. Sci 19:(1-2):11

Coenen M. (2001) Feeding horses after surgery. Ubersichten zur Tierernahrung 29:180-187.

Cotter R, Taylor C A, et. al. (1987) A metabolic comparison of a pure long chain triglyceride emulsion (LCT) and various medium-chain triglyceride ((MCT)-LCT combination emulsion in dogs. American Jr. of Clinical Nutrition 45:927-939.

Crozier G L (1988) Medium chain triglycerides feeding over the long term. The metabolic fate of (14 c) octanoate and (14 c) oleate in isolated rat hepatocyte J Nutr. 118:297.

Damle B C et. al., (2002) Effect of food on the oral bioavailability of diadnosine from encapsulated enteric-coated beads. J. Clin Pharmacol 42:419-427.

Duggan C., Gannon, J. And Walker W A (2002) Protective nutrients and functional foods for the gastrointestinal tract. The American Journal of Clinical Nutrition. 75: 789-808.

Eaton H D, Rousseau J E, Hall R C, Frier H I, Lucas J J. (1972) Reevaluation of the minimum vitamin A requirement of Holstein calves based upon elevated cerebrospinal fluid pressure. Jr. of Dairy Science. 55:232.

Friend, B A et. al. (1984) Nutritional and therapeutic aspects of *Lactobacilli*. J. Appl. Nutr. 36: 125-133.

Friend T H (2000) Dehydration, Stress and water consumption of horses during long distance commercial transport. J Animal Science 78:2568-2580.

Feedlot Management (1986) A vitamin boost for incoming calves. May. Feedlot Management, p26.

Galyean M. L, L. J. Perino and G. C. Duff (1999). Interaction of Cattle/Immunity and Nutrition. J.Anim. Sci.1999.77: 1120-1134.

Gardemann A., Watanbe Y., Grobe, V., Hesse, S., Jungermann K. (1992) Increase in intestinal glucose absorption and hepatic glucose uptake elicited by luminal but not vascular glutamine in the jointly perfused small intestine and liver of the rat. Biochem J. 283:759-765.

Gerald, S. (1983) Rocky Top Cattle Company Probiotic Study Apr. 6, 1983.

Griffiths R D, Jones C and Palmer T E. (1997) Six-month outcome of critically ill patients given glutamine-supplemented parenteral nutrition. Nutrition 13:295-302.

Grancer D et. al. (1987) Studies on the tolerance of medium chain tridglycerides in dogs. J Parenter Enteral Nutr. 11:280-6.

Halseth A E, et. al. (1998) Regulation of hepatic glutamine metabolism during exercise in the dog. Am. J. Physiol. Endocrinol. Metab. 275:E655-E664.

Hays, V. S., D. R. Gill, R. A. Smith, and R. L. Ball. (1987). The effect of vitamin e supplementation on performance of newly received stocker cattle. Okla. Agric. Exp. Sta. MP-119. pp 198-201. Oklahoma State Univer., Stillwater.

Humbert B., Nguyen, P., Dumon, H., Deschamps, Y J., Darmon D. (2002). Does enteral glutamine modulate whole-body leucine kinetics in hypercatabolic dogs in a fed state? Metabolism, Clinical and Experimental 51:628-635.

Hutcheson David.(1984) Combating transportation stress. Feedlot Management. October, p10.

Jank M (2004) Nutrition of dogs and cats with cancer. Part II: food supplements for ill animals. Zycie Weterynaryjne 79:85-87.

Kenyon C J et. al. (1998) The use of pharmacoscintigraphy to elucidate food effects observed with a novel protease inhibitor (saquinavir). Pharm Res 15:417-422.

Klaenhammer T R et al. (1988) Bacteriocins of lactic acid bacteria. Biochimie 70:337-349.

Krehbiel C. R., S. R. Rust, G. Zhang, and S. E. Gilliland. (2003). Bacterial direct fed microbials in ruminant diets: Performance response and mode of action. J.Anim, Sci. 81 (E. Suppl.2):E120-E132.

Kweon M N, et. al. (1991) Effect of alanylglutamine-enriched infusion on tumor growth and cellular immune function in rats. Amino Acis 1:7-16.

Lee H. F., Chiang S H, and Lee H F (1994) Energy value of medium-chain triglycerides and their efficacy in improving survival of neonatal pigs. J. Animal Science 72:133-138.

Lepine A J, Body R D, Welch J A and Ronecker K R (1989) Effects of colostrum or medium chain triglycerides supplementation on the pattern of plasma glucagon, non-esterified fatty acids and survival of neonatal. J Animal Sci 69:983.

Loerch, S C, and Fluharty F L (1999) Physiological changes and digestive capabilities of newly received feedlot cattle. J Anim. Sci. 77:1113-1119.

Marahrens, M., et al. Special problems of long distance road transport of cattle. (2003) Deutsche Tierarztliche Wochenschrift 110: 120-125.

Meier-Hellmann A, Reinharty K, Bredle D and Sakka S G. 2001 Therapeutic Options for the Treatment of impaired gut function. J Am Soc. Nepherol 12:S65-S69.

Miller, A L. (1999) Therapeutic considerations of L-glutamine: A review of the literature. Altern Med. Rev. 4:239-248.

Mizock B A, and Demichele S J (2004). The acute respiratory distress syndrome role of nutritional modulation of inflammation through dietary lipids. Nutrition in Clinical Practice 19:563-574.

Newsholme E A Crabtree, B., Ardawi M S A. (1985) The role of high rates of glycolysis and glutamine utilization in rapidly dividing cells. Biosci. Rep. 4:393-400.

Newsholme R, Gordon S, Newholem Ea. (1987) Rates of utilization and fates of glucose, glutamine, pyruvate, fatty acids and ketone bodies by mouse macrophages. Biochem J. 242:631-636.

Nockel, C. F., (1996) Antibiotics improve cattle immunity following stress. Animal Feed Science. 71:2539-2545.

Olgilvie G K 2003 Nutrition and Cancer: New keys for cure and control 2003. 28th World small animal veterinary association proceedings.

Pastores S. Et. Al. (1994) Immunomodulatory effects and therapeutic potential of glutamine in the critically ill patient. Nutrition 10:385-391.

Perino, L. J. 1992. Overview of the bovine respiratory disease complex. Compend. Cont. Educ. Pract. Vet.14:S3-S6.

Pizzorno J. (1996) Total Wellness (Prima Publishing).

Plaiser J C, Wakton J P, Mcbride B W (2001) Effect of post-ruminal infusion of glutamine on plasma amino acids, milk yield and composition in lactating dairy cows. Can. J. Animal Science 81:229-235.

Price, D (1984) The rumen in the feedlot. Feedlot Management. October, p16.

Ramamoorthy P., Thomas S., Balasubramanian K A. (2003) Oral glutamine attenuates surgical manipulation in the intestinal brush border membrane. Journal of Surgical Research. 115:148-156.

Rastall (Rasta Ra. (2004) Bacteria in the gut: friends and foes and how to alter balance. Journal of Nutrition. 134:2022S-20226S.

Reecy J M et. Al (1996) The effect of postruminal amino acid flow on muscle cell proliferation and protein turnover. J. Animal Science 74:2158-2169.

Rhoads J M et. al. (1991) L-glutamine stimulates jejunal sodium and chloride absorption in pig rotavirus enteritis. Gastroenterology 100:683-91.

Rivera, J. D., G. C. Duff, M. L. Galyean, D. A. Walker, and G. A. Nunnery. (2002) Effects of supplemental vitamin E on performance, health and humoral immune response of beef cattle. J.Anim. Sci.80; 933-941.

Roth E. et. al. (1988) Alanylglutamine reduces muscle loss of alanine and glutamine in postoperative anaesthetized dogs. J Clin Sci. 75:641-648.

Rotting A K, Freeman, D E, Constable, P D, Eurell J A C, and Wallig M A (2004) Effects of phenylbutazone, indomethicin, prostaglandin E2, and glutamine on restitution of oxidant-injured right dorsal colon of horses in vitro. American Journal of Veterinary Research. 65:1589-1596.

Scheltinga M R et. al. (1991) Glutamine-enriched intravenous feeds attenuate extracellular fluid expansion after a standard stress. Ann. Surg 214:385-393.

Sata H (1994) Plasma ketone levels in neonatal calves fed medium chain triglycerides in milk. J Vet Med Sci. 56:781-782.

Sata H and Tsunkishi E (1993) Effects of medium chain triglycerides feeding on blood metabolite levels and fiber digestion in steers Anim. Sci. Techno. (Jpn) 64:623-628.

Scheltinga M R et. al. (1991) Glutamine-enriched intravenous feeds attenuate extracellular fluid expansion after a standard stress. Ann. Surg 214:385-393.

Selye, H (1946) The general adaptation syndrome and the diseases of adaptation. Journal of Clinical Endocrinology 6: 117.

Souba, W., Smith R. J. and Wilmore, D. W. (1985). Glutamine metabolism by the intestinal tract. J Parenter. Enteral. Nutr. 9:608-617.

Souba, W., (1993) Intestinal glutamine metabolism and nutrition. Jr. Nutritional Biochemistry 4:2-9.

Silva A C, et. al. (1998) Efficacy of a glutamine-based oral rehydration solution on the electrolyte and water absorption in a rabbit model of secretory diarrhea induced by cholera toxin. J. Pediatr. Gastroenterol Nutr. 26:513-9.

Spada C et. al., (2002) Evaluation of antiretroviral therapy associated with alpha tocopherol supplementation in HIV-infected patients. Clin Chem Lab Med 40:456-459.

Stewart R L. Cochran/Pioneer Field Demonstration. 30 day Ryegrass trial. Miss. State University AC 601/325-2851.

Strueder V A, et. al (1993). Effects of prepartum propylene glycol administration on prepartum fatty acid liver in dairy cows. J Dairy Sci. 76:2931.

Thorn, James (1985) Why vaccines sometimes fail. Feedlot Management. May, p15.

Van Zyl C G, Lamber E V et. al (1996) Effects of medium chain triglycerides ingestion on fuel metabolism and cycling performance. J Appl. Physiol. 80:2217-2225.

Ward, M P, et al (2004) A randomized clinical trial using probiotics to prevent *Salmonella* faecal shedding in hospitalized horses. Journal of Equine Veterinary Science. 24:242-247.

Wilmore D W, Sharbert J K (1998) Role of glutamine in immunologic responses. Nutrition 14:618-626.

Windmueller H. G, (1982). Glutamine utilization by the small intestines. Adv. Enzymology 53:202-231.

Weese J S and Arryo L. (2003) Bacteriological evaluation of dog and cat diets that claim to contain probiotics. Can Vet J. 44:212-215.

Weese J S et al. (2004) Screen of the equine intestinal microflora for potential probiotic organisms. Equine Veterinary Journal 36: 351-355.

Wischmeyer P E. (2003) Clinical applications of L-glutamine: past, present and future. Nutrition in clinical Practice. 18:377-385.

Young V R and Ajami A M (2001) Glutamine: the emperor or his clothes. Jr. of Nutrition 131:2449S-2459S.

Yoshida S, et al. (1992) Effect of glutamine supplementation on lymphocyte function in septic rats. J. Parent Enterol. Nutri 16: 305.

Yuyama T et al (2004) Evaluation of a host-specific lactobacillus probiotic in neonatal foals. Journal of Applied Research in Veterinary Medicine. 2:26-33.

Zaloga G P (2005) Improving outcomes with specialized nutrition support. Jr. of Parenteral and Enteral Nutrition 29: S49-S52

What is claimed is:

1. A nutritive feed composition having therapeutic effects in an animal for maintaining and enhancing gastrointestinal microflora, the rehydration status, energy balance and the immune system consisting of:
   a. probiotics, wherein the probiotics consist of yeast, *Lactobacillus* species, and *Enterococcus* species and wherein the probiotics are in an active dose of $10^7$ to $10^{11}$ colony forming units (CFU) per day;
   b. prebiotics, wherein the prebiotics are selected from the group consisting of inulin or soy fructo-oligosaccharide and wherein the prebiotic is used in the composition from concentrations of about 0.01 to 10% (w/w);
   c. glutamine or glutamine analog, wherein the concentration of the glutamine or glutamine analog is from 44 mg to 100 mg grams/kilogram body weight;
   d. glucose, wherein the concentration of glucose is from 10 to 50 grams/kilogram of body weight;
   e. glycine, wherein the concentration of glycine is 66 mg to 264 mg/kilogram of body weight;
   f. electrolytes, wherein the electrolytes are selected from the group consisting of sodium chloride and potassium chloride and wherein the concentration of the electrolytes are from 5 mg to 100 mg/kilogram of body weight;
   g. vitamins, wherein the vitamins include vitamin A in a concentration from 50-300 IU/kilogram bodyweight, vitamin E in a concentration of 0.5 IU/kilogram bodyweight, folic acid in a concentration from 0.5 to 2 IU/kilogram bodyweight, and vitamin $D_3$ in a concentration from 5-30 IU/kilogram bodyweight;
   h. minerals, wherein the minerals include zinc in a concentration from 100 mg to 200 mg/kilogram bodyweight, copper in a concentration from 0.1 to 2 mg/kilogram bodyweight, manganese in a concentration from 0.05 to 0.2 mg/kilogram bodyweight;
   i. medium chain triglycerides, wherein the concentration of medium chain triglycerides is from 100 mg to 600 mg/kilogram bodyweight and wherein the medium chain triglycerides contain acyl chain lengths from 8 to 10 carbons; and
   j. wherein elements a-i are in a unit dosage form in a delivery system and the delivery system is selected from the group consisting of boluses, tablets, chewable tablets, capsules, powders, suspensions, gels, or pastes.

* * * * *